(12) United States Patent
Kasthurirangan et al.

(10) Patent No.: US 9,211,061 B2
(45) Date of Patent: Dec. 15, 2015

(54) SYSTEM AND METHOD FOR EVALUATING INTRAOCULAR LENS PERFORMANCE

(71) Applicant: Abbott Medical Optics Inc., Santa Ana, CA (US)

(72) Inventors: Sanjeev Kasthurirangan, Fremont, CA (US); Patricia Ann Piers, Groningen (NL); Hendrik A. Weeber, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/098,845

(22) Filed: Dec. 6, 2013

(65) Prior Publication Data

US 2014/0160436 A1    Jun. 12, 2014

Related U.S. Application Data

(60) Provisional application No. 61/734,240, filed on Dec. 6, 2012.

(51) Int. Cl.
*A61B 3/02* (2006.01)
*A61B 3/032* (2006.01)
*A61B 3/00* (2006.01)
*A61B 3/10* (2006.01)

(52) U.S. Cl.
CPC .............. *A61B 3/032* (2013.01); *A61B 3/0025* (2013.01); *A61B 3/10* (2013.01)

(58) Field of Classification Search
CPC .................................. A61B 3/10; A61B 3/032
USPC .................. 351/200, 222, 239, 246
See application file for complete search history.

(56) References Cited

U.S. PATENT DOCUMENTS

| 5,652,640 | A | 7/1997 | Schneider et al. |
| 8,596,787 | B2 * | 12/2013 | Dai ............................... 351/212 |
| 2007/0052927 | A1 | 3/2007 | Noda et al. |
| 2009/0281552 | A1 | 11/2009 | Hiramatsu et al. |

(Continued)

FOREIGN PATENT DOCUMENTS

| EP | 0810427 A1 | 12/1997 |
| WO | WO-2012052585 A1 | 4/2012 |

OTHER PUBLICATIONS

International Search Report and Written Opinion for Application No. PCT/US2013/073514, mailed on Mar. 27, 2014, 10 pages.

(Continued)

*Primary Examiner* — Tuyen Tra
(74) *Attorney, Agent, or Firm* — Abbott Medical Optics Inc.

(57) ABSTRACT

Systems and methods for providing improved techniques for evaluating performance of intraocular lenses. Such techniques can be used to evaluate lens designs and can help reduce the need for multiple clinical trials that may otherwise be needed to evaluate multiple design iterations. In one embodiment, a method is provided for method for evaluating performance of an intraocular lens, where the method comprises capturing a plurality of images through the intraocular lens at different focus positions; displaying at least one selected image from the plurality of images to a test subject; receiving input from the test subject indicative of perceived acuity of the at least one selected image; and determining a measure of intraocular lens performance from the received input.

12 Claims, 6 Drawing Sheets

(56) References Cited

U.S. PATENT DOCUMENTS

2010/0082017 A1* 4/2010 Zickler et al. ............... 606/4
2011/0080562 A1* 4/2011 Iizuka et al. ............ 351/233

OTHER PUBLICATIONS

Brainard D.H., The Psychophysics Toolbox, Spatial Vision, vol. 10, pp. 433-436.

Gobbi P.G., et al., "Far and Near Visual Acuity with Multifocal Intraocular Lenses in an Optomechanical Eye Model with Imaging Capability," Journal of Cataract and Refractive Surgery, 2007, vol. 33 (6), pp. 1082-1094.

Gobbi P.G., et al., "Optomechanical Eye Model with Imaging Capabilities for Objective Evaluation of Intraocular Lenses," Journal of Cataract and Refractive Surgery, 2006, vol. 32 (4), pp. 643-651.

Kim M.J., et al., "Objective Evaluation of Through-Focus Optical Performance of Presbyopia-Correcting Intraocular Lenses Using an Optical Bench System," Journal of Cataract and Refractive Surgery, 2011, vol. 37 (7), pp. 1305-1312.

Norrby S., et al., "Model Eyes for Evaluation of Intraocular Lenses," Applied Optics, 2007, vol. 46(26), pp. 6595-6605.

Peli E., et al., "Appearance of Images Through a Multifocal Intraocular Lens," Journal of the Optical Society of America, 2001, vol. 18 (2), pp. 302-309.

* cited by examiner

SYSTEM AND METHOD FOR EVALUATING INTRAOCULAR LENS PERFORMANCE

CROSS-REFERENCES TO RELATED APPLICATIONS

This application claims priority to U.S. provisional application No. 61/734,240 filed on Dec. 6, 2012, the entire contents of which are incorporated herein by reference.

TECHNICAL FIELD

Embodiments of the present invention relate to vision treatment techniques and in particular, to ophthalmic lenses such as intraocular lenses (IOLs).

BACKGROUND OF THE INVENTION

Intraocular Lenses (IOLs) may be used for restoring visual performance after a cataract surgery or other ophthalmic procedure in which the natural crystalline lens is replaced with or supplemented by implantation of an IOL. A variety of different types of IOLs are currently available, including monofocal and multifocal IOLs, phakic IOLs and piggyback IOLs (i.e. IOLs implanted in an eye already having an IOL). In general, monofocal IOLs are intended to provide vision correction at one distance only, usually the far focus. In contrast, multifocal IOLs use two foci, one near and one far, optionally with some degree of intermediate focus. Such multifocal, or bifocal, IOLs are intended to provide good vision at two distances, and include both refractive and diffractive multifocal IOLs.

One significant issue is the cost and/or time needed to develop and evaluate new IOL designs. Visual performance of IOLs, including multifocal IOLs, is usually evaluated through human clinical trials with surgical implantation. Development of a new type of IOL may need multiple design iterations requiring multiple clinical trials which may prove costly and time consuming.

Therefore, what is needed are improved techniques for evaluating the performance of intraocular lenses (IOLs) to reduce the need for invasive and time consuming clinical trials.

BRIEF SUMMARY OF THE INVENTION

Embodiments of the present invention generally provide improved techniques for evaluating performance of intraocular lenses. Such techniques can be used to evaluate lens designs and can help reduce the need for multiple clinical trials that may otherwise be needed to evaluate multiple design iterations. In one embodiment, a method is provided for evaluating performance of an intraocular lens, where the method comprises capturing a plurality of images through the intraocular lens at different focus positions; displaying at least one selected image from the plurality of images to a test subject; receiving input from the test subject indicative of perceived acuity of the at least one selected image; and determining a measure of intraocular lens performance from the received input. In another embodiment, a system is provided for evaluating performance of an intraocular lens, where the system comprises an image capture mechanism, a display screen, and a processing system. In this embodiment the image capture mechanism is configured to capture a plurality of images through the intraocular lens at different focus positions. The display screen is configured to display at least one selected image from the plurality of images to a test subject. Finally, the processing system is configured to receive input from the test subject indicative of perceived acuity of the at least one selected image determine a measure of intraocular lens performance from the received input.

For a fuller understanding of the nature and advantages of the present invention, reference should be had to the ensuing detailed description taken in conjunction with the accompanying drawings.

It should be noted that the geometries shown in certain aforementioned figures were not drawn exactly to scale. For example, the heights of the profiles shown in the figures may vary depending on factors such as the amount of correction needed by the patient, the refractive index of the lens material and surrounding medium, and the desired phase shift/delay.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity and brevity, many other elements found in typical ophthalmic lenses, implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments of the present invention encompass systems and methods that provide improved techniques for evaluating lens performance over an extended range of focal points or foci. Systems and methods disclosed herein can be applied to various types of ophthalmic lenses such as, for example, contact lenses, intraocular lenses, spectacle lenses, and corneal inlays or onlays. Exemplary embodiments include various types of intraocular lenses, including monofocal lenses, lenses having an extended depth of focus, multifocal intraocular lenses, etc. Furthermore, embodiments of the present invention may be used with monofocal diffractive or refractive lenses, bifocal diffractive or refractive lenses, and multifocal diffractive or refractive lenses.

Figure 9:
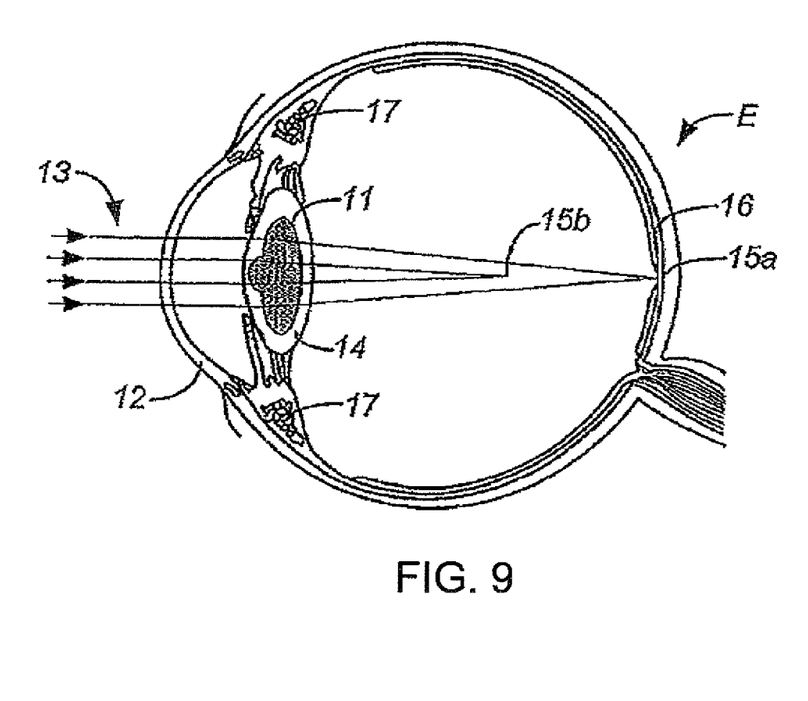
FIG. 9 is a cross-sectional view of an eye with a multifocal refractive intraocular lens.

Turning now to FIG. 9 a cross-sectional view of an eye E fit with a multifocal IOL 11 is illustrated. As shown, multifocal IOL 11 may, for example, comprise a bifocal IOL. Multifocal IOL 11 receives light from at least a portion of cornea 12 at the front of eye E and is generally centered about the optical axis of eye E. For ease of reference, FIG. 9 does not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens.

In a young healthy eye, contraction and relaxation of ciliary muscles 17 surrounding the capsular bag 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore conventionally use corrective optics having two optical powers, one for near vision and one for far vision, as provided by multifocal IOL 11.

Multifocal lenses may optionally also make special use of the refractive properties of the lens. Such lenses generally include different powers in different regions of the lens so as to mitigate the effects of presbyopia. For example, as shown in FIG. 9 a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

It should be noted that the multifocal IOL 11 illustrated in FIG. 9 is just one example of the type of lens that can be evaluated using the systems and methods described herein. For example, the systems and methods can be applied to lenses with spherical aberration to improve optical image quality, extended depth of focus (i.e. increased range of functional focus without discrete far and near focal points), accommodating IOLs where at least one aspect of the IOL is capable of responding to ciliary muscle movements during near viewing, spatially varying optical properties to generally improve optical quality of visual function.

The embodiments described herein generally provide improved techniques for evaluating performance of intraocular lenses, such as the multifocal IOL 11 illustrated in FIG. 9. Such techniques can be used to evaluate lens designs and can help reduce the need for multiple clinical trials that may otherwise be needed to evaluate multiple design iterations. In one embodiment, a method is provided for method for evaluating performance of an intraocular lens, where the method comprises capturing a plurality of images through the intraocular lens at different focus positions; displaying at least one selected image from the plurality of images to a test subject; receiving input from the test subject indicative of perceived acuity of the at least one selected image; and determining a measure of intraocular lens performance from the received input. In another embodiment, a system is provided for evaluating performance of an intraocular lens, where the system comprises an image capture mechanism, a display screen, and a processing system. In this embodiment the image capture mechanism is configured to capture a plurality of images through the intraocular lens at different focus positions. The display screen is configured to display at least one selected image from the plurality of images to a test subject. Finally, the processing system is configured to receive input from the test subject indicative of perceived acuity of the at least one selected image determine a measure of intraocular lens performance from the received input.

Figure 1:
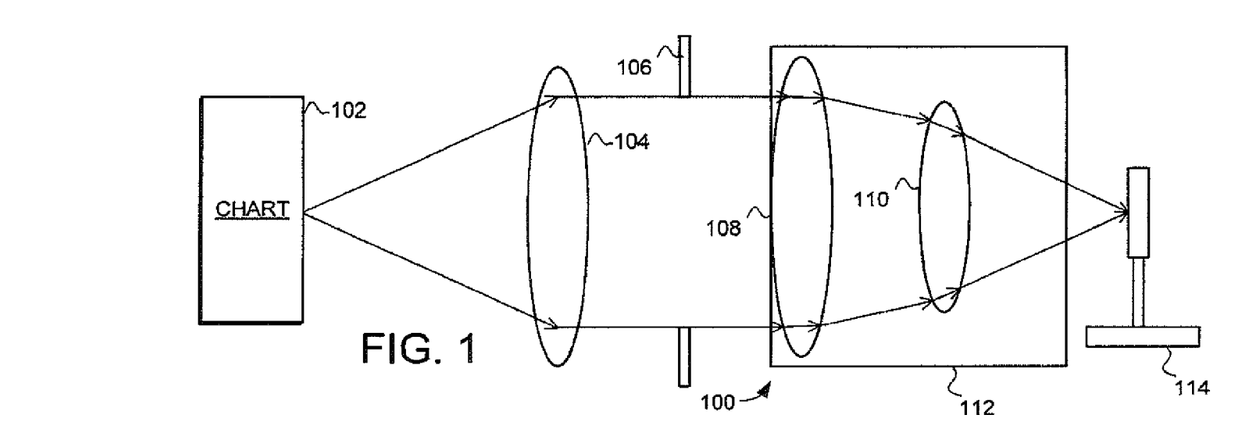
FIGS. 1, 2 and 3 are cross-sectional side views of an image capturing system for capturing images though an intraocular lens in accordance with an embodiment of the invention.

Turning now to FIG. 1, a cross-sectional side view of an image capturing system 100 for capturing images though an intraocular lens in accordance with an embodiment of the invention is illustrated. The image capturing system 100 includes a collimating lens 104, an aperture 106, a cornea lens 108, an intraocular lens 110, an aqueous solution 112, and a sensor 114. The imaging capturing system 110 is configured to capture an image of the chart 102 using the sensor 114. It is important to note that image of the chart 102 is captured through the intraocular lens 110 that is under evaluation. It is also important to note that the system 110 captures these images in a way that models the performance of the intraocular lens 110 when it is implanted in the human eye. Specifically, the collimating lens 104, aperture 106, cornea lens 108 and aqueous solution 112 are all preferably selected to provide a test environment which mimics the human eye in which the intraocular lens 110 is designed to be implanted.

As one example, the image capturing system can be designed to use the Average Cornea Eye (ACE) Model. The ACE Model is based on studies and wavefront measurements of the human eye, with the aperture 106, cornea lens 108 and aqueous solution 112 chosen to model the corresponding features of the human eye. For example, the cornea lens 108 is chosen to have spherical aberration and chromatic aberration that mimics the human cornea. Likewise, the aqueous solution 112 is chosen to have refractive index difference similar to that found in the human eye. Finally, the aperture 106 can be configured to provide different sizes to mimic different entrance pupil diameters. For example, the aperture 106 can be configured to provide the equivalent of 3 mm and 5 mm pupil diameters. As another example, different aperture sizes from 2 mm to 6 mm diameter can be used to evaluate performance at different pupil sizes (e.g., to simulate day and night conditions). For more information on the ACE model see: Norrby, S., Piers, P., Campbell, C., & van der Mooren, M. (2007) Model eyes for evaluation of intraocular lenses. Appl Opt, 46 (26), 6595-6605, the content of which is incorporated herein by reference.

It should be noted that the ACE model is just one type of model that could be implemented in the image capturing system, and that other models could be used. For example, the physiological model eye, also described in the above referenced paper can also be used.

As was noted above, the image capturing system 100 is configured to capture images through the intraocular lens 110. The sensor 114 is preferably selected to provide high resolution images. For example, the sensor 114 is preferably selected to capture at least 12-bit grayscale images of the chart 102. A variety of different types of sensors can thus be utilized, including charge coupled device (CCD) based sensors. For example, a PL-H9611A camera available from PixeLINK, Ontario, Canada can be used.

Figure 2:
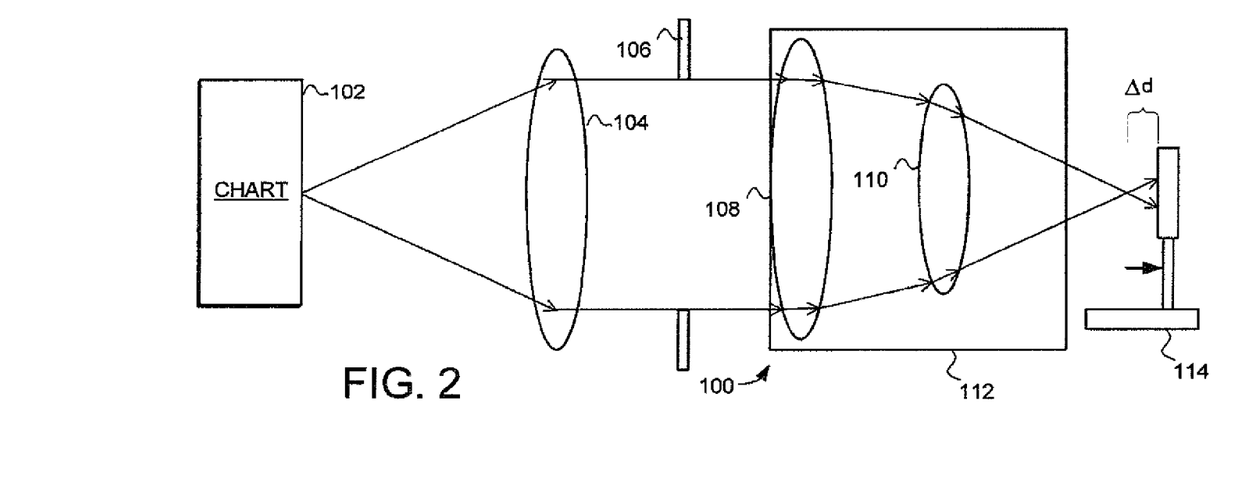
Figure 3:
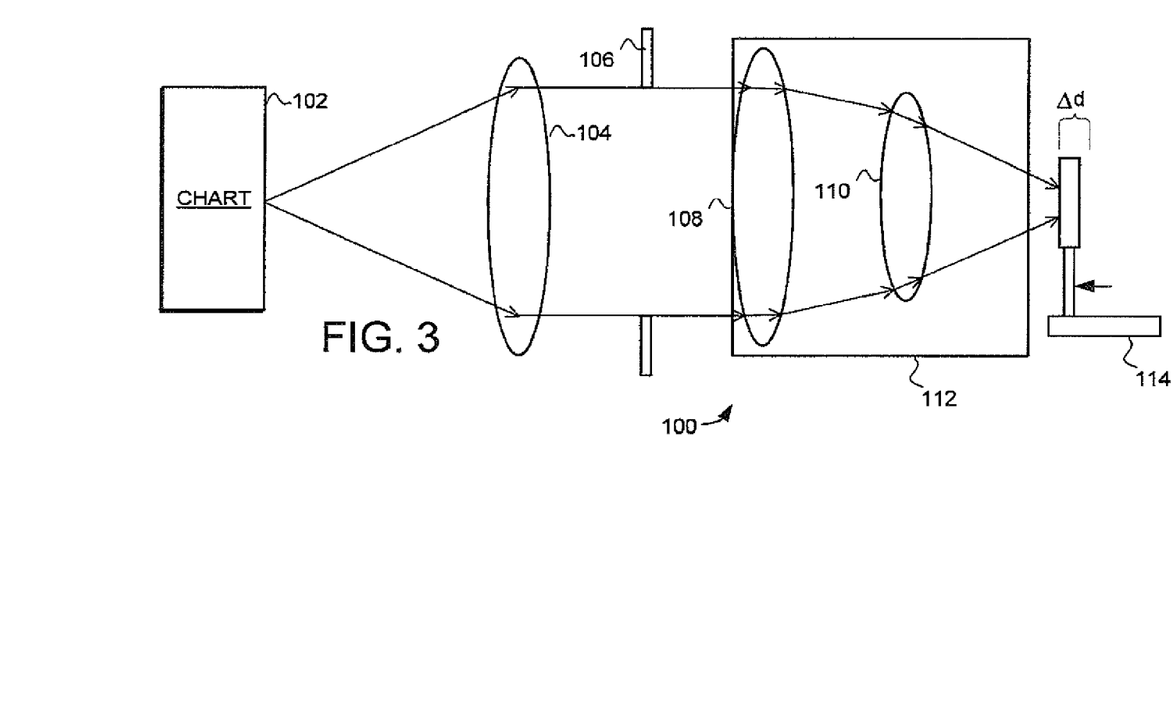

As was noted above, the image capturing system 100 is configured to capture images at different focus positions. In the embodiment of FIGS. 1-3, the system 100 can accomplish this by moving the sensor 114 relative to the intraocular lens 110. This motion of the sensor 114 allows for images to be taken at different levels of defocus. For example, FIG. 2 shows the system 100 with the sensor 114 moved further away from the intraocular lens 110, while FIG. 3 shows the system 100 with the sensor 114 moved closer to the intraocular lens 110. In both cases moving the sensor allows images to be taken at different levels of focus. As one specific example, the system 100 can be configured to take images at levels of defocus from approximately +0.75 to −3.50 D in 0.25 D steps.

As was noted above, the image capturing system 100 is configured to capture images through the intraocular lens 110. Specifically, the image capturing system 100 is configured to capture images of all or part of the chart 102. The chart 102 can comprise any combination of shapes and symbols. As one example, the chart 102 comprises all or part of characters from an Early Treatment of Diabetic Retinopathy Study (ETDRS) chart. The captured images can then be used to determine the performance of the intraocular lens based on feedback from a test subject. For example, by displaying one or more characters from the captured chart to a test subject and measuring the ability of the test subject to distinguish the orientation or content of the characters.

Figure 4:
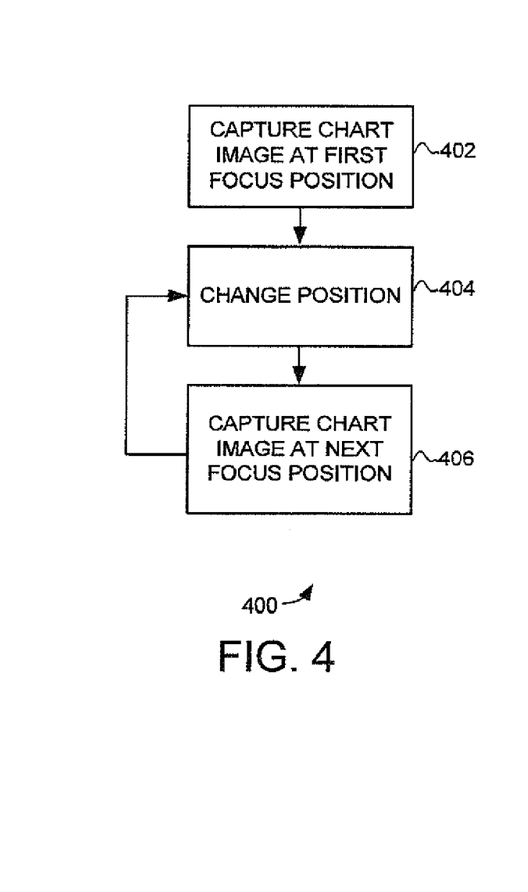
FIG. 4 is a flow diagram illustrating a method for capturing images through an intraocular lens in accordance with an embodiment of the invention.

Turning now to FIG. 4, a flow diagram illustrates a method 400 for capturing images through an intraocular lens. The first step 402 is to capture a chart image at a first focus position. As described above, a variety of different devices and models can be used to capture a chart image at a first focus position, including the system 100 illustrated in FIGS. 1-3.

Figure 7:
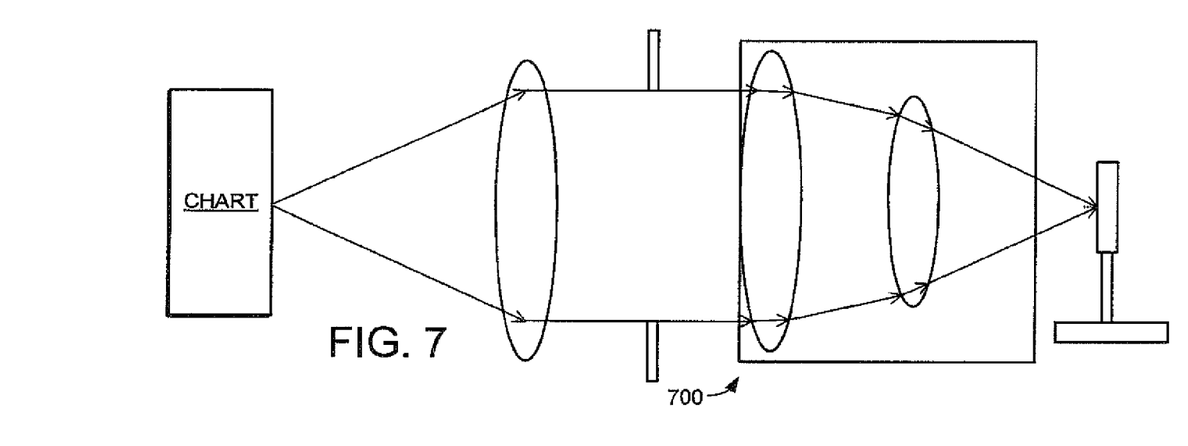
FIGS. 7 and 8 are cross-sectional side views of an image capturing system for capturing images though an intraocular lens in accordance with another embodiment of the invention.
Figure 8:
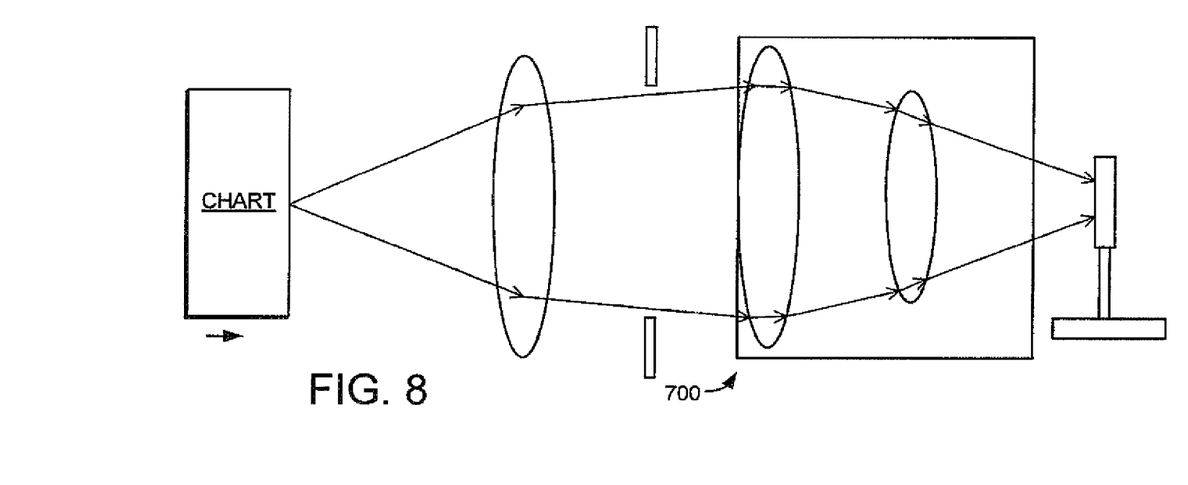

The next step 404 is to change focus position. In one embodiment, this can be accomplished by changing the position of the sensor relative to the intraocular lens. An example of this was illustrated in the system of FIGS. 1, 2 and 3. In another embodiment, the change in focus position is accomplished by changing the position of the source chart relative to the image capturing system. An example of this system is illustrated in FIGS. 7 and 8. In either case it will generally be desirable to change focus position in uniform steps of defocus. For example, by changing focus in 0.25 D steps.

With the focus position changed, the next step 406 is to capture another chart image. The method then returns to step 404 where the focus is changed again, and then another image captured in step 406. This process is continued until images are captured at each of the desired levels of focus. Typically, the range and focus distance between images will be determined based on the intraocular lens being evaluated. For example, a typical multifocal lens may have images captured at different defocus levels from +0.75 to −3.50 D, in 0.25 D steps and an extended depth of focus lens may have images captured at different defocus levels from +0.75 to −2.00 D, in 0.25 D steps and a monofocal lens to improve optical quality at best focus may have images captured only at the 0.0 D Turning now to FIG. 5, a flow diagram illustrates a method 500 for determining a measure of intraocular lens performance. In general, the method 500 displays all or part of a captured images to a test subject, receives a series of inputs from the test subject indicative of whether or not the images can be visually distinguished, and determines a measure of the intraocular lens performance from the inputs. The first step 502 is to select a chart image corresponding to a focus position. The next step 504 is to display the chart image to the test subject at different sizes. In generally, the test image should be displayed to a user in a way that accurately represents the visual characteristics of the captured image. For example, by displaying the image using the same format in which it was captured. As one specific example, by displaying the image using 12 bit gray scale image processing when then image was originally captured to 12 bit gray scale.

Figure 5:
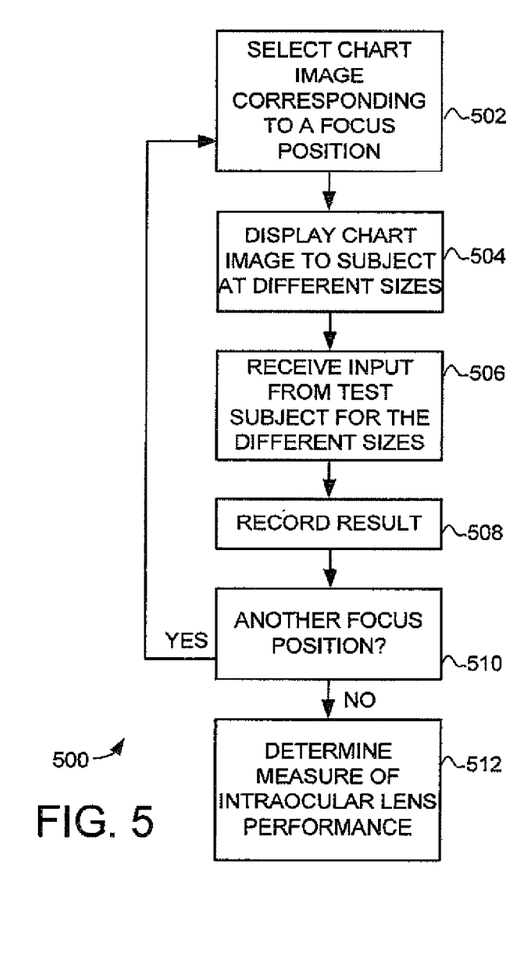
FIG. 5 is a flow diagram illustrating a first method for determining a measure of intraocular lens performance in accordance with an embodiment of the invention.

The next step 506 is to receive input from the test subject for the different sizes. The next step 508 is to record the results. The next step 510 is to determine if there is a chart image for another focus position. If there is another chart the method returns to step 502 and proceeds again. This process is continued until chart images have been displayed at different sizes and user input has been received for each focus position. Then the method proceeds to step 512 and a measure of the intraocular lens performance is determined.

As one example of how method 500 can be implemented, a single character from each chart image can be cropped and scaled to different sizes using a tool such as MatLab (The Mathworks, Natick, Mass.). The character can then be randomly oriented and displayed to the test subject, and the test subject prompted to indicate the perceived orientation of the letter as input (for example, using the psychophysics toolbox and a 4-alternative forced choice psychophysical procedure, e.g., see Brainard, D. H. (1997) The Psychophysics Toolbox, Spatial Vision 10:433-436 and Pelli, D. G. (1997) The VideoToolbox software for visual psychophysics: Transforming numbers into movies, Spatial Vision 10:437-442.). For example the letter "E" can be displayed and the user prompted to indicate the one of four alternative orientations of "E" they perceive. If the perceived orientation is correct, the same or different letter is randomly oriented and displayed to the user at a smaller size. This process can be continued until the smallest size letter that can be distinguished by the user is determined. This process can be then repeated for the images captured at each focal position. Thus, the visual acuity of the images for each focal position can be determined. And from this, a measure of the intraocular lens performance can be determined as the visual acuity at different levels of focus. Typically with a multifocal IOL one can except good visual acuity and far and near focal planes with reduced visual acuity in the intermediate focal planes.

As another example a word or phrase from each chart image can be cropped and scaled to different sizes to judge reading comprehension ability through the intraocular lens. Specifically, complex charts words, sentences can be used to measure more functional performance as opposed to a simple acuity tests. Functional tests may include reading speed (i.e. maximum speed with which a sentence can be read), critical print size (i.e. print or image size smaller than which reading speed begins to decline). As another example, the images can be displayed at different contrast levels to better simulate intraocular performance under different visual conditions. For example, the chart can be made with different contrast (high 100% contrast or low 10% or 5% contrast) to evaluate IOL performance under impoverished conditions (i.e. low contrast).

Figure 6:
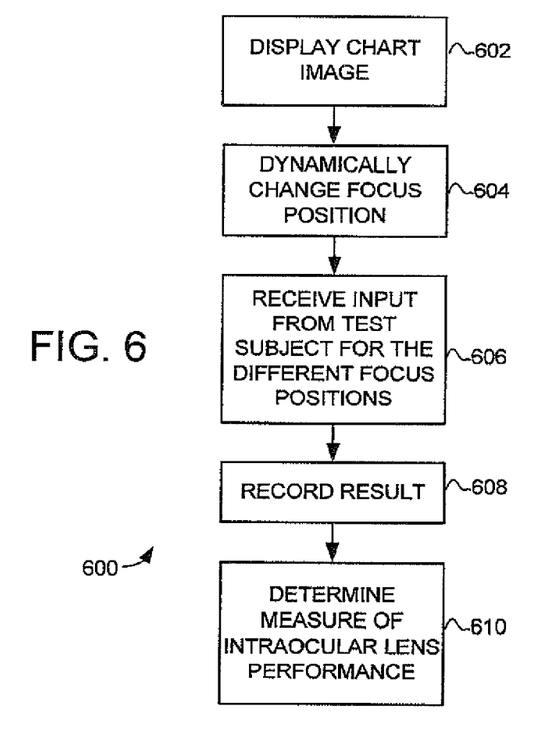
FIG. 6 is a flow diagram illustrating a second method for determining a measure of intraocular lens performance in accordance with an embodiment of the invention.

Turning now to FIG. 6, a flow diagram illustrates a second method 600 for determining a measure of intraocular lens performance. In general, the method 600 displays all or part of a chart image while dynamically changing the focus position, receives a series of inputs from the test subject indicative of whether or not the images can be visually distinguished, and determines a measure of the intraocular lens performance from the inputs. The first step 602 is to select a chart image. The next step 604 is to display the chart image to the test subject while dynamically changing the focus position.

The next step 606 is to receive input from the test subject for the different focus positions. The next step 608 is to record the results. The next step 610 is to determine a measure of the intraocular lens performance.

As one example of how method 600 can be implemented, a chart image displayed to the test subject while the focus position is dynamically changed, and the test subject prompted to indicate when the image is not distinguishable by the user. This process can be continued for different size characters until the smallest size character that can be distinguished by the user is determined for each focus position. Thus, the visual acuity of the images for each focal position can be determined. And from this, a measure of the intraocular lens performance can be determined.

Example

Photographic images of a miniature ETDRS chart in a bench-top eye model (Average Cornea Eye (ACE) model) that has a cornea lens with the same spherical aberration as the average human cornea were obtained for a multifocal IOL (ZM900, Abbott Medical Optics, USA) and a monofocal control lens (CeeOn, Abbott Medical Optics, USA). Images were obtained in 12-bit grayscale at different defocus levels from +0.75 to −3.50 D, in 0.25 D steps, by adjusting the camera position, and for two different entrance pupil diameters of the ACE model (3 mm and 5 mm). A central 'S' letter from the ETDRS chart was cropped and scaled to different sizes for visual acuity testing using Matlab (The Mathworks, USA), psychophysics toolbox and the QUEST procedure with 4-alternative forced choice. The letter was presented on a CRT monitor (NEC MultiSync FP2141SB, Mitsubishi Electronics, Illinois) through a BITS # device (Cambridge Research Systems, UK). Visual acuity testing was performed from 0 D to 3 D defocus (in 0.50 D steps) binocularly in two observers with no prior ocular surgery and 20/20 visual acuity. The results were compared to the data from a FDA clinical trial on the two IOLs.

Results:

Visual acuity for different defocus levels of the 'S' letter was 20/20 at 0 D for both IOLs (mean±SD; 911A: −0.03±0.0 log MAR, ZM900: 0.01±0.01 log MAR) and declined with defocus for both IOLs, but returned to 20/20 at 3 D with the multifocal IOL (ZM900: 0.0±0.02 log MAR). The through focus visual acuities with the multifocal IOL were similar for 3 mm and 5 mm apertures (all differences were within 1-line or 0.1 log MAR). When compared to clinical trial data, visual acuities with the multifocal IOL were within 1-line (or 0.1 log MAR) for all defocus levels.

Thus, the embodiments described herein provide improved techniques for evaluating performance of intraocular lenses. Such techniques can be used to evaluate lens designs and can help reduce the need for multiple clinical trials that may otherwise be needed to evaluate multiple design iterations.

While the exemplary embodiments have been described in some detail, by way of example and for clarity of understanding, those of skill in the art will recognize that a variety of modification, adaptations, and changes may be employed. Hence, the scope of the claims should not be limited to the description of the preferred versions contained herein.

What is claimed is:

1. A method for evaluating performance of an intraocular lens, the method comprising:
   capturing a plurality of images of a source chart through the intraocular lens at different focus positions;
   displaying at least one selected image from the plurality of images to a test subject;
   receiving input from the test subject indicative of perceived acuity of the at least one selected image; and
   determining a measure of intraocular lens performance from the received input.

2. The method of claim 1 wherein the step of capturing the plurality of images through the intraocular lens at different focus positions relative to the intraocular lens comprises moving an image sensor between captures.

3. The method of claim 1 wherein the step of capturing the plurality of images of the source chart through the intraocular lens at different focus positions relative to the intraocular lens comprises moving the source chart between captures.

4. The method of claim 1 wherein the step of capturing the plurality of images through the intraocular lens comprises capturing through an average cornea eye (ACE) model.

5. The method of claim 1 wherein the step of capturing the plurality of images through the intraocular lens comprises capturing through different aperture sizes to simulate day and night vision.

6. The method of claim 1 wherein the step of displaying at least one selected image from the plurality of images comprises displaying a character from the at least one selected image at a selected orientation.

7. The method of claim 1 wherein the step of displaying at least one selected image from the plurality of images comprises displaying a word from the at least one selected image.

8. The method of claim 1 wherein the step of displaying at least one selected image from the plurality of images comprises displaying the image at different contrasts.

9. The method of claim 1 wherein the step of displaying at least one selected image from the plurality of images comprises displaying a portion of the least one selected image at different sizes to the test subject.

10. The method of claim 1 wherein the receiving input from the test subject comprises receiving input indicating a perceived orientation of a character in the image.

11. The method of claim 1 wherein the step of determining the measure of intraocular lens performance from the received input comprises determining the smallest size of a character in an image corresponding to a focus position that can be visually distinguished by the test subject from the received user input.

12. A system for evaluating performance of an intraocular lens, the system comprising:
   an image capture mechanism configured to capture a plurality of images of a source chart through the intraocular lens at different focus positions;
   a display screen configured to display at least one selected image from the plurality of images to a test subject; and
   a processing system configured to receive input from the test subject indicative of perceived acuity of the at least one selected image, and determine a measure of intraocular lens performance from the received input.

* * * * *